United States Patent [19]
Winslow et al.

[11] Patent Number: 6,033,405
[45] Date of Patent: *Mar. 7, 2000

[54] APPARATUS AND METHOD FOR IMPLANT INSERTION

[75] Inventors: Charles J. Winslow, Walnut Creek; Steven T. Mitchell, Pleasant Hill, both of Calif.

[73] Assignee: Surgical Dynamics, Inc., Norwalk, Conn.

[*] Notice: This patent is subject to a terminal disclaimer.

[21] Appl. No.: 09/033,984

[22] Filed: Mar. 3, 1998

Related U.S. Application Data

[63] Continuation-in-part of application No. 08/354,364, Dec. 12, 1994, abandoned, which is a continuation-in-part of application No. 08/306,879, Sep. 15, 1994, abandoned.

[51] Int. Cl.[7] ........................................................ A61F 2/44
[52] U.S. Cl. .................................................................. 606/61
[58] Field of Search ............................... 606/61, 99, 100, 606/73, 72, 104, 86; 623/17

[56] References Cited

U.S. PATENT DOCUMENTS

| | | | |
|---|---|---|---|
| 4,950,270 | 8/1990 | Bowman et al. | 606/72 |
| 5,489,307 | 2/1996 | Kuslich et al. | 623/17 |
| 5,782,919 | 7/1998 | Zdeblick et al. | 623/17 |

Primary Examiner—Michael Buiz
Assistant Examiner—William Lewis

[57] ABSTRACT

Apparatus for and methods of inserting implants are disclosed wherein the apparatus includes a handle portion and a body portion attached to the handle portion and defining a longitudinal axis. The body portion includes an outer tubular member fixed relative to the handle portion for rotation therewith about the longitudinal axis. The outer tube member has first implant engaging structure adjacent a distal end. An inner tubular member is disposed at least partially within the outer tubular member and is mounted for longitudinal motion relative to the outer tubular member. Second implant engaging structure is positioned adjacent a distal end of the inner tubular member. The body portion further includes an inner shaft, coaxially mounted at least partially within the inner tubular member for independent rotation relative to the inner and outer tubular members, the inner shaft having third implant engaging structure adjacent a distal end. In a method for inserting an implant having a hollow portion with a closed distal end and a removable cap, the first, second and third implant engaging structures are attached to the implant with at least one of the engaging structure attached to the removable cap and another of the engaging structure attached to the hollow portion. The implant is preferably preloaded with bone chips and/or bone growth inducing substances prior to attachment. Thereafter, the preloaded implant is inserted into the desired surgical location.

6 Claims, 10 Drawing Sheets

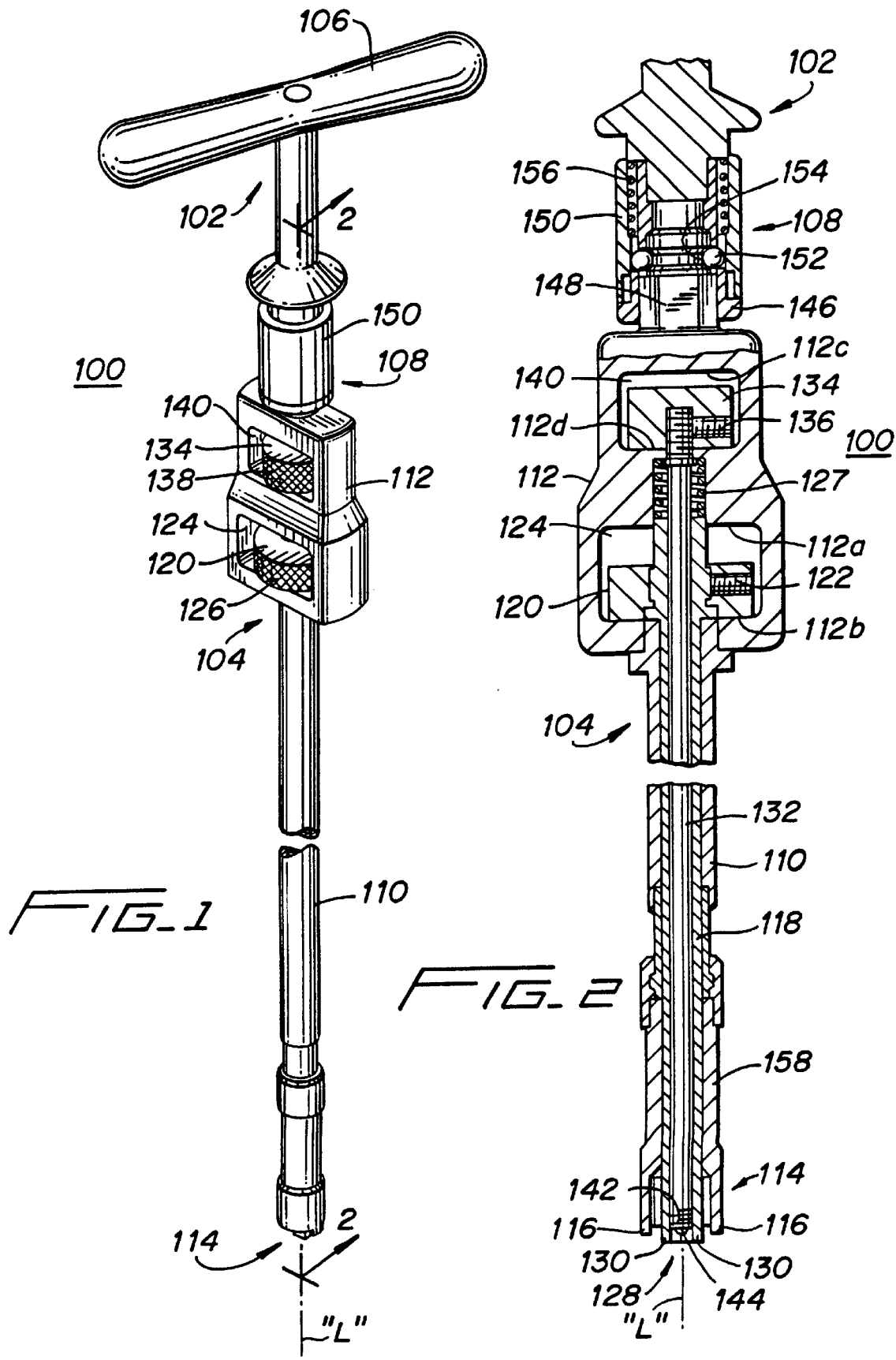

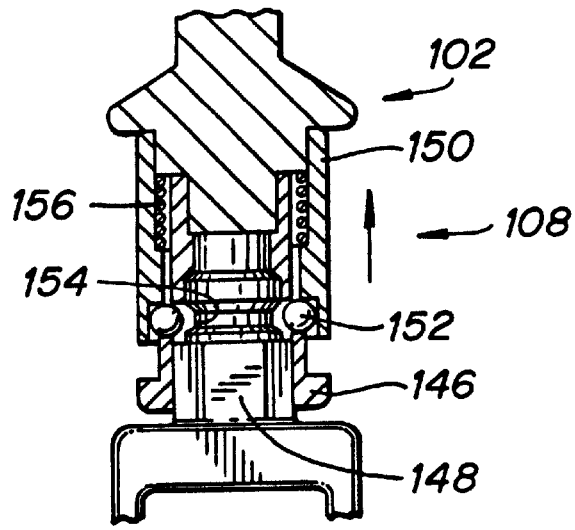
FIG_2A
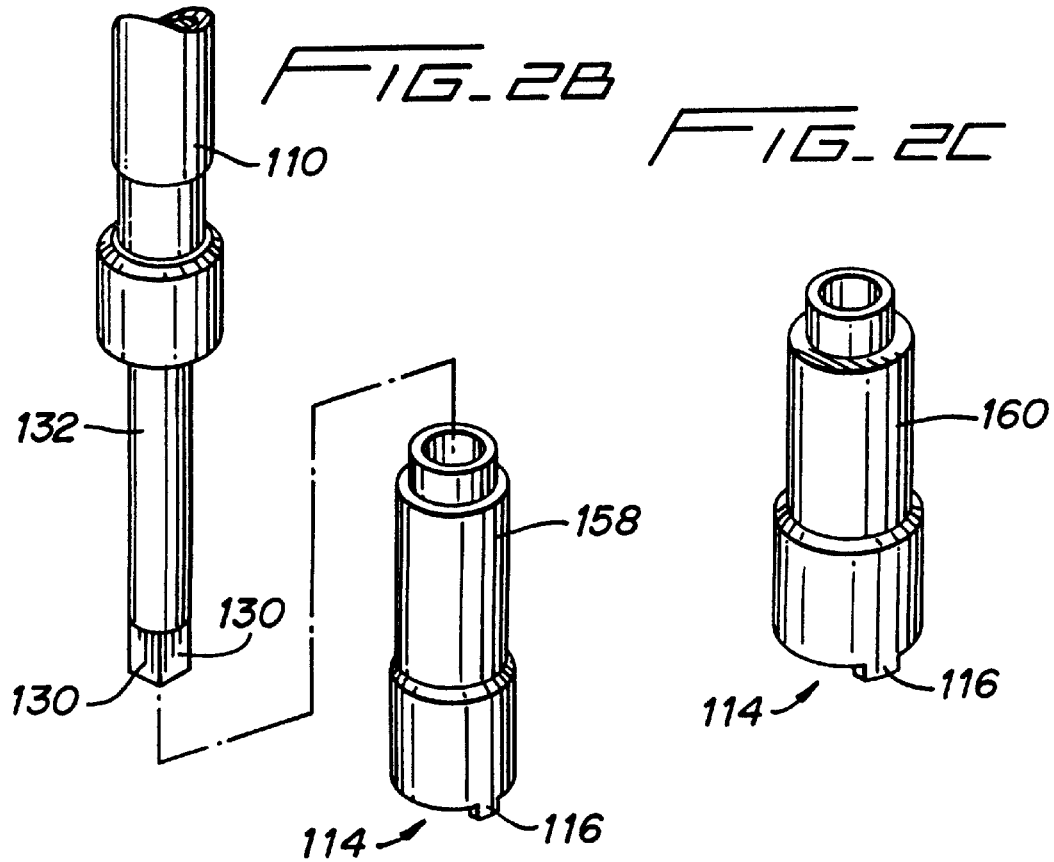
FIG_2B
FIG_2C

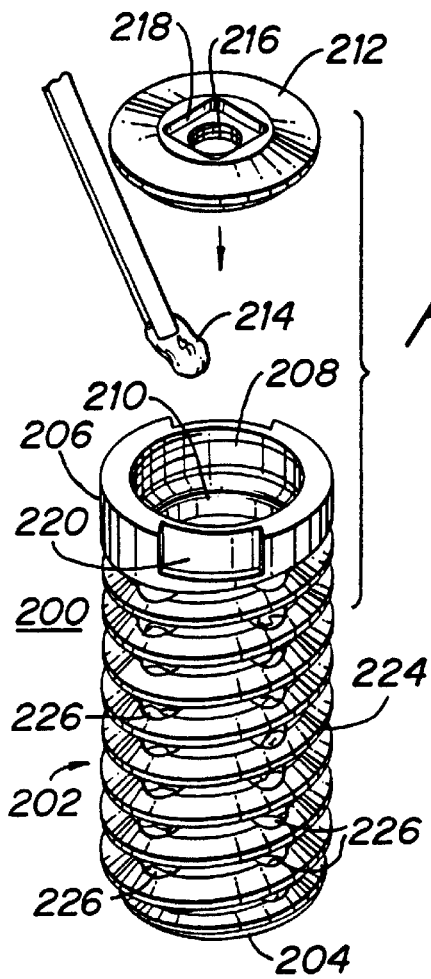
FIG_6
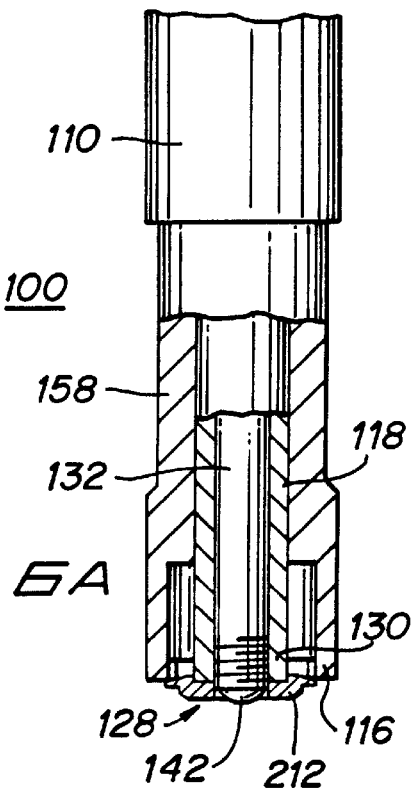
FIG_6A
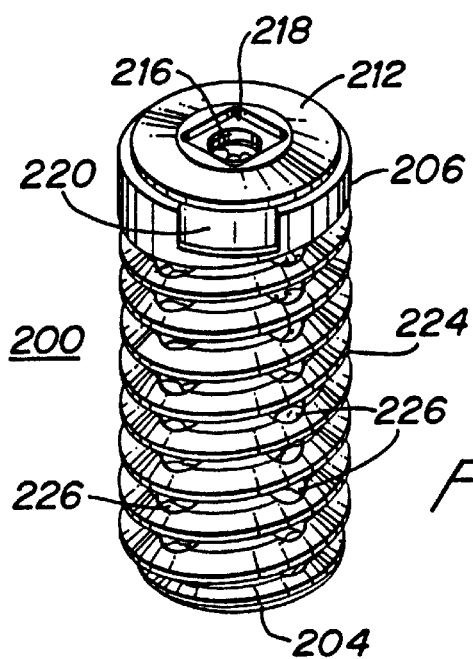
FIG_7

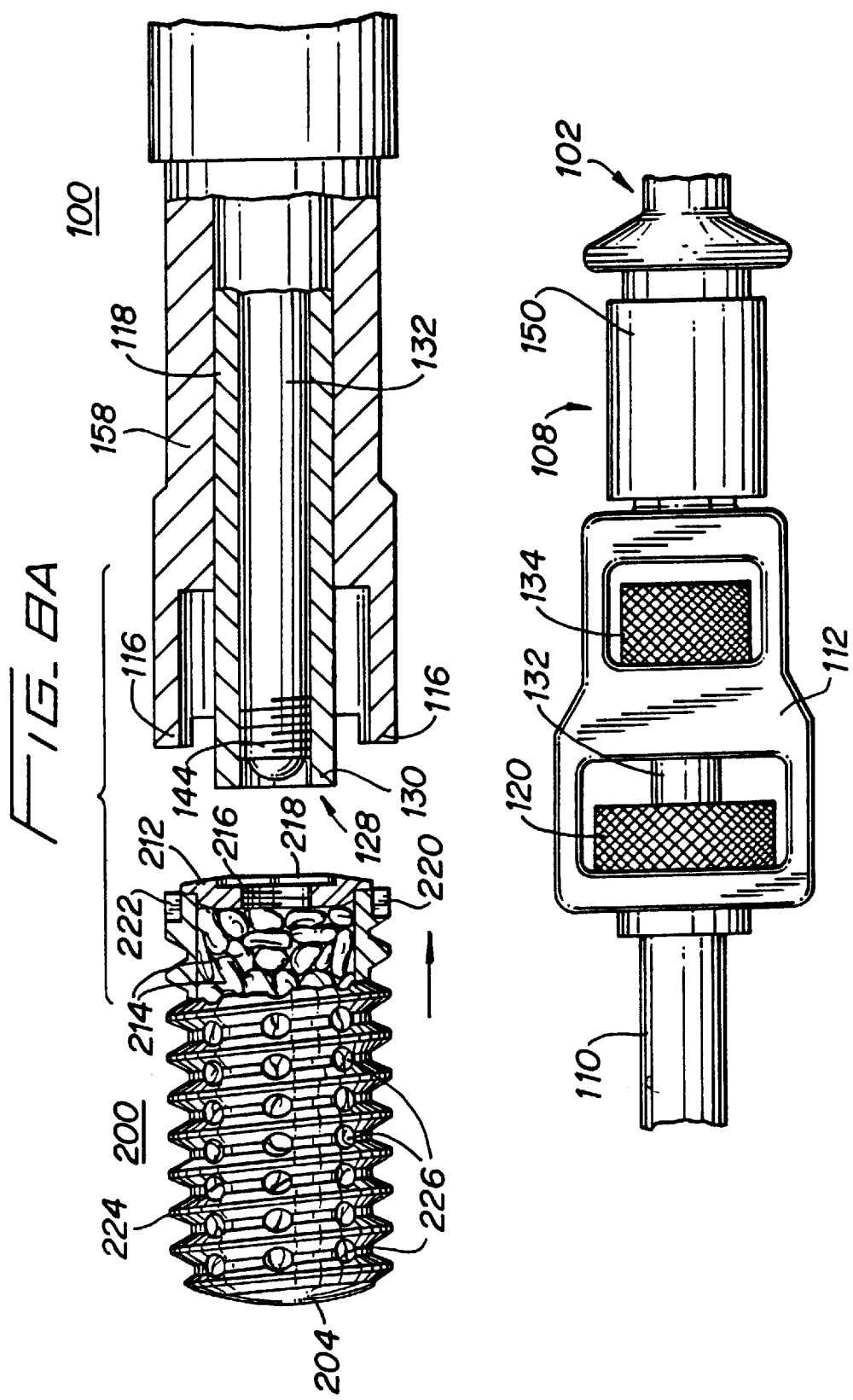

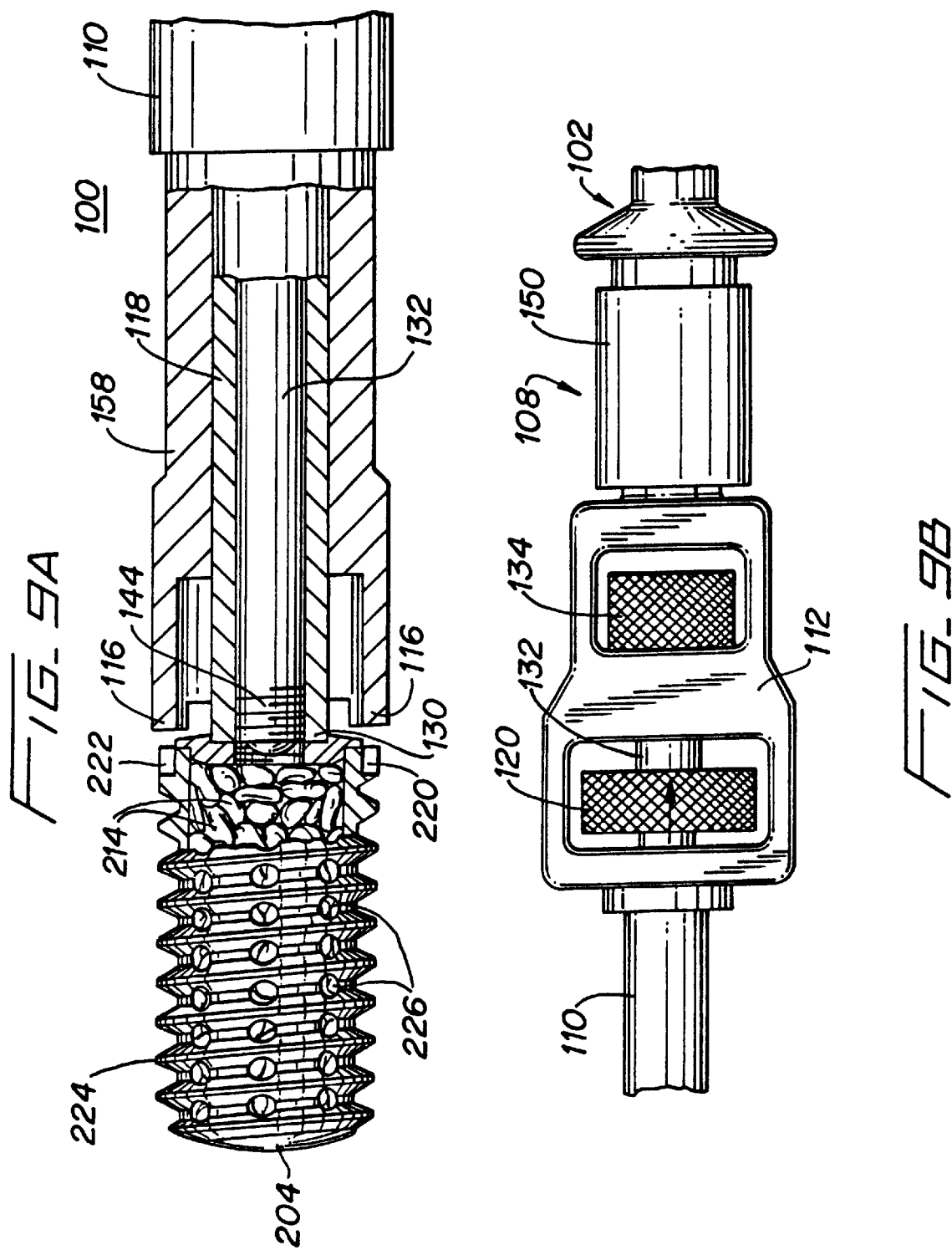

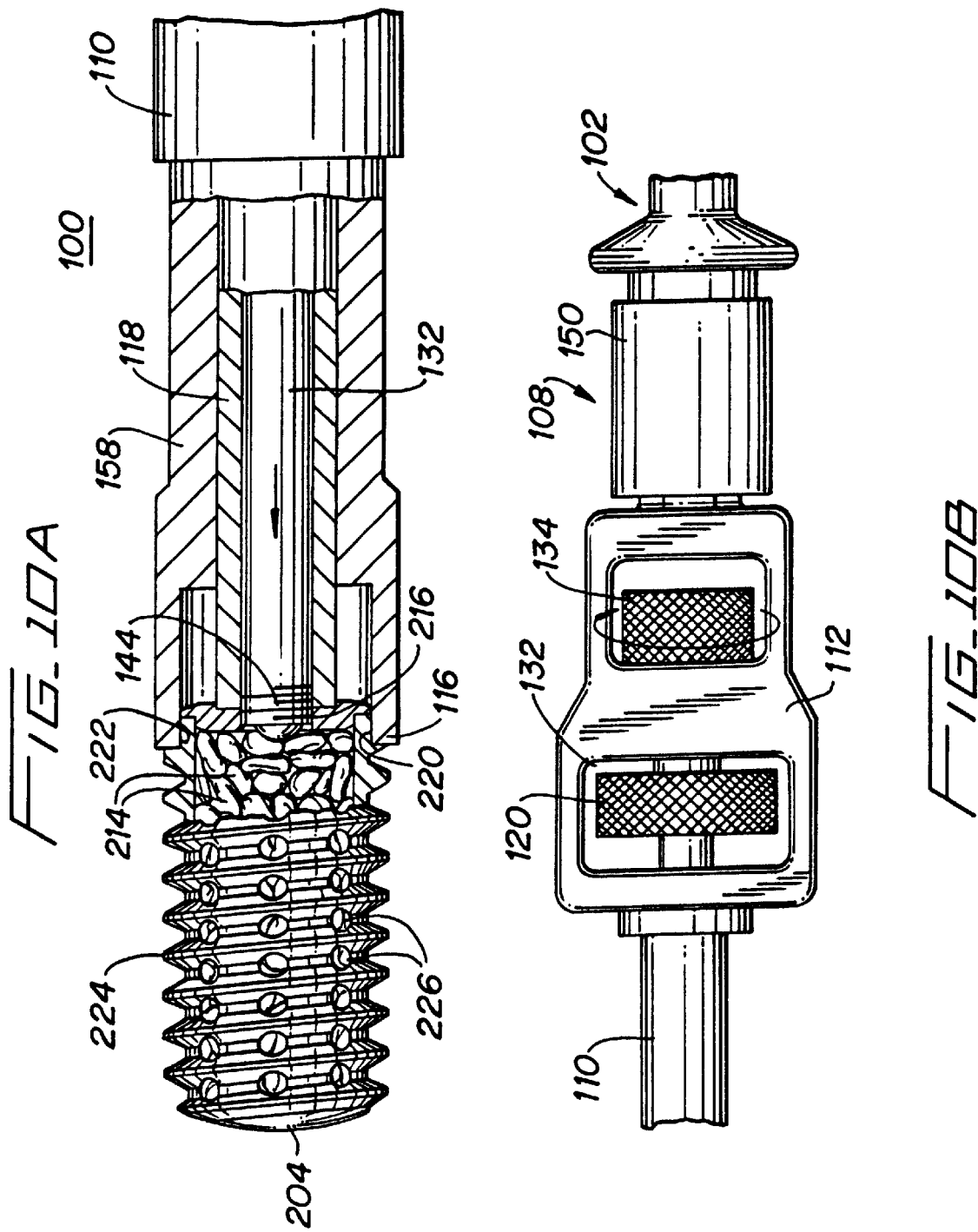

APPARATUS AND METHOD FOR IMPLANT INSERTION

This application is a continuation-in-part of U.S. application Ser. No. 08/354,364, filed on Dec. 12, 1994, now abandoned, which is a continuation-in-part of U.S. application Ser. No. 08/306,879, filed on Sep. 15, 1994, now abandoned. The contents of these applications are incorporated herein by reference.

BACKGROUND

1. Technical Field

This disclosure relates generally to apparatus and methods for implant insertion. More particularly, to apparatus and methods for insertion of implants to facilitate fusion of adjacent bony structure.

2. Background of the Related Art

A large number of orthopedic procedures involve the insertion of either natural or prosthetic implants into bone or associated tissues. These procedures include, for example, ligament repair, joint repair or replacement, non-union fractures, facial reconstruction, spinal stabilization and spinal fusion. In a typical procedure, an insert, dowel or screw is inserted into a prepared bore formed in the bone or tissues to facilitate repair and healing. See, for example, U.S. Pat. Nos.: 5,470,334 to Ross et al.; 5,454,811 to Huebner, 5,480,403 to Lee et al.; 5,40,805 to Warren; 5,358,511 to Gatturna et al.; and 4,877,020 to Vich.

Some implants are particularly configured with cavities and bores to facilitate bony ingrowth and enhance anchoring of the implant at the insertion site. See, for example, U.S. Pat. Nos.: 4,328,593 to Sutter et al.; 4,936,851 to Fox et al.; and 4,878,915 to Brantigan. Implants in the form of fusion cages having internal cavities to receive bone growth stimulation materials such as bone chips and fragments are disclosed, for example, in U.S. Pat. Nos.: 4,501,269 to Bagby; 4,961,740 to Ray et al.; 5,015,247 to Michaelson; and 5,489,307 to Kuslich et al. These types of implants are particularly well suited for intervertebral spinal fusion procedures necessitated by injury, disease or some degenerative disorder of the spinal disc. Subsequently, there may be progressive degeneration leading to mechanical instability between adjacent vertebrae necessitating direct fusion of the vertebrae while maintaining a pre-defined intervertebral space. This fusion may be accomplished by the insertion of one or more of the specialized implants as discussed above and also discussed in commonly assigned U.S. Pat. No. 5,026,373, incorporated herein by reference.

Both anterior (transabdominal) and posterior surgical approaches are used for interbody fusions of the lumbar spine. Fusions in the cervical area of the spine are primarily done using an anterior approach. Typically, an implant such as a plug, dowel prosthesis or cage is inserted into a preformed cavity inside the interbody, interdiscal space. Since it is desirable in these procedures to promote a "bone to bone" bridge, connective tissue and at least a portion of the discal tissue is removed. Preferably, relatively deep cuts are made in the adjacent bones in order to penetrate into the softer, more vascularized cancerous region to facilitate bone growth across the implant.

When installing these specialized implants, an insertion tool is used to position the implant in the desired intervertebral location. See, for example, U.S. Pat. Nos.: 3,848,601 to Ma et al.; 4,501,269 to Bagby; 4,877,020 to Vich; and 4,878,915 to Brantigan. Once in position, the insertion tool is removed and, where the implant structure permits, bone chips or other bone growth inducing substances are packed into the implant in vivo. Subsequently, an end cap or other sealing structure is positioned to close the implant. See, for example, commonly assigned U.S. Pat. No. 4,961,740 to Ray et al. incorporated herein by reference.

Typical insertion tools use either a single implant engagement structure or, at most, two implant engagement structures to facilitate positioning of the implant. For example, in U.S. Pat. No. 4,501,269 to Bagby, prongs are used to engage the implant. In U.S. Pat. Nos. 4,878,915 to Brantigan and 5,015,247 to Michaelson, a threaded rod and slot are used to engage the implant. In U.S. Pat. Nos.: 4,961,740 to Ray et al.; 5,489,308 and 5,489,307, both to Kuslich et al.; and 4,936,838 to Bagby, a single central shaft is used. In all of these insertion tools, no structure is provided to permit the insertion tool to attach to an outer peripheral portion of the implant, either in vitro or in vivo. Further, these tools do not provide structure which separately engages both the implant and the implant closure, e.g. an end cap.

Accordingly, a need exists for an insertion tool which is capable of either inserting an implant preloaded with bone chips, etc. Such in vitro packing facilitates the surgical procedure because it is often time consuming and relatively difficult, especially for example in cervical applications, to pack the cage in vivo. It would also be advantageous if such insertion tool could be additionally used to insert/position an empty implant for subsequent in vivo packing and closure.

SUMMARY

Apparatus for and methods of inserting implants are disclosed wherein the apparatus includes a handle portion and a body portion attached to the handle portion and defining a longitudinal axis. The body portion includes an outer tubular member fixed relative to the handle portion for rotation therewith about the longitudinal axis. The outer tubular member has first implant engaging structure adjacent a distal end. An inner tubular member is disposed at least partially within the outer tubular member and is mounted for longitudinal motion relative to the outer tubular member. Second implant engaging structure is positioned adjacent a distal end of the inner tubular member. The body portion further includes an inner shaft, coaxially mounted at least partially within the inner tubular member for independent rotation relative to the inner and outer tubular members, the inner shaft having third implant engaging structure adjacent a distal end In a method for inserting an implant having a hollow portion with a closed distal end and a removable cap, the first, second and third implant engaging structures are attached to the implant with at least one of the engaging structures attached to the removable cap and another of the engaging structure attached to the hollow portion. The implant is preferably preloaded with bone chips and/or bone growth inducing substances prior to attachment. Thereafter, the preloaded implant is inserted into the desired surgical location.

BRIEF DESCRIPTION OF THE DRAWINGS

Various embodiments of the subject implant insertion apparatus are described below with reference to the drawings wherein:

FIG. 1 is a perspective view of an implant insertion apparatus constructed in accordance with a preferred embodiment of the subject disclosure:

FIG. 2 is a side view in cross-section of the implant insertion apparatus taken along line 2—2 of FIG. 1;

FIG. 2A is an enlarged side view in cross-section of the connection between the handle portion and the body portion of the implant insertion apparatus of FIG. 1;

FIG. 2B is an enlarged perspective view of the distal ends of the outer and inner tubular members of the implant insertion apparatus of FIG. 1;

FIG. 2C is an enlarged perspective view of an interchangeable distal end of the outer tubular member of the implant insertion apparatus of FIG. 1;

FIG. 6 is an enlarged perspective view of the implant of FIG. 3 with parts separated and loading of bone chips in process;

FIG. 6A is a side view in partial cross-section showing an end cap mounted to the inner tubular member and the inner shaft;

FIG. 7 is a perspective view of a preloaded implant with removable end cap in place;

FIG. 8A is an enlarged side view in partial cross-section illustrating the distal end of the implant insertion apparatus of FIG. 1 and the implant of FIG. 7;

FIG. 8B is an enlarged side view of the housing and rotation wheels of the body portion illustrating the relative position of the inner tubular member as shown in FIG. 8A;

FIG. 9A is an enlarged side view in partial cross-section illustrating the distal end of the implant insertion apparatus of FIG. 1 with the second and third implant engagement structure attached to the removable cap of the implant of FIG. 7;

FIG. 9B is an enlarged side view of the housing and rotation wheels of the body portion illustrating the relative position of the inner tubular member and the inner shaft as shown in FIG. 9A;

FIG. 10A is an enlarged side view in partial cross-section illustrating the distal end of the implant insertion apparatus of FIG. 1 with the first, second and third implant engagement structure attached to the implant of FIG. 7;

FIG. 10B is an enlarged side view of the housing and rotation wheels of the body portion illustrating the relative position of the inner shaft, the inner tubular member and the outer tubular member as shown in FIG. 10A;

DETAILED DESCRIPTION OF PREFERRED EMBODIMENTS

Figure 3:
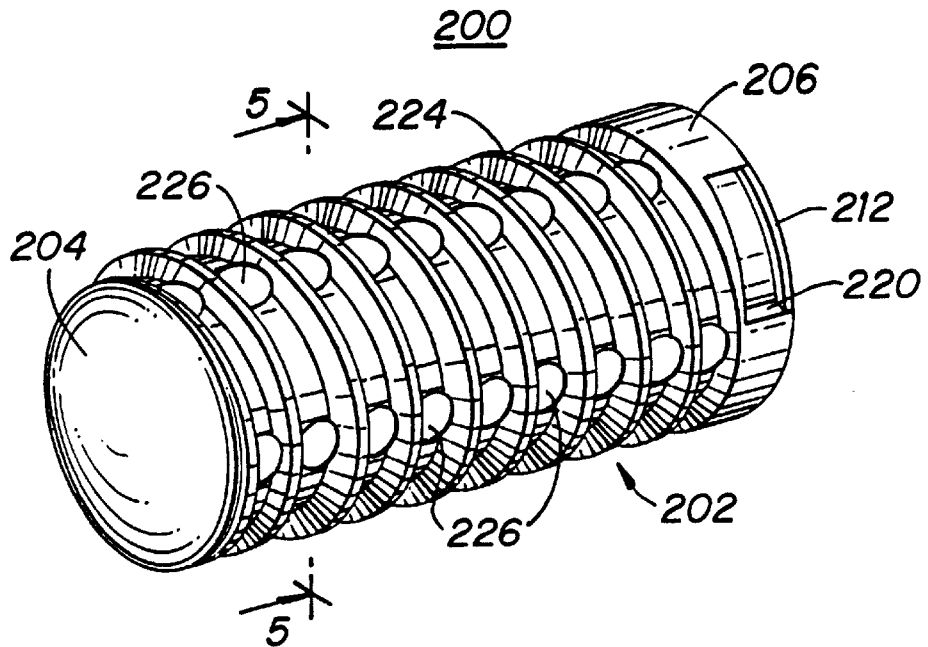
FIG. 3 is an enlarged perspective view of one type of implant configured for interbody fusion.

The preferred embodiments of the apparatus and methods disclosed herein are discussed in terms of orthopedic spinal fusion procedures and apparatus. It is also envisioned, however, that the disclosure is applicable to a wide variety of procedures including, but not limited to ligament repair, joint repair or replacement, non-union fractures, facial reconstruction and spinal stabilization. In addition, it is believed that the present apparatus finds application in both open and minimally invasive procedures including endoscopic and arthroscopic procedures wherein access to the surgical site is achieved through a cannula or small incision.

In the description which follows, the term "proximal", as is traditional will refer to the portion of the structure which is closer to the operator, while the term "distal" will refer to the portion which is further from the operator.

Referring now in detail to the drawings in which like reference numerals identify similar or identical elements, a preferred embodiment of the implant insertion apparatus is illustrated in FIGS. 1 and 2 and is designated generally by reference numeral 100. Implant insertion apparatus 100 includes a removable handle portion 102 and a body portion 104. Handle portion 102 has a T-handle 106 positioned at a proximal end and releasable engagement structure 108 at a distal end thereof.

Body portion 104 defines a longitudinal axis "L" and includes an outer tubular member 110 fixed to a housing 112 for longitudinal rotation therewith. First implant engaging structure 114 is positioned adjacent a distal end of outer tubular member 110. Outer tubular member 110 preferably includes a removable distal end portion 158 described below. In the embodiment shown, the implant engaging structure is a pair of distally extending tabs 116 projecting from the distal end of outer tubular member 110.

Body portion 104 further includes an inner tubular member 118 disposed at least partially within outer tubular member 110. Inner tubular member 118 is mounted for limited longitudinal motion relative to outer tubular member 110 and is independently rotatable relative to outer tubular member 110 by wheel 120. In the illustrated embodiment, set screw 122 anchors wheel 120 to the inner tubular member 118. A first cavity 124 is defined in housing 112 and is dimensioned to limit the relative longitudinal motion of inner tubular member 118 by confining wheel 120 between walls 112a, 112b. As shown in FIG. 1, the periphery of wheel 120 may be provided with knurling 126 to enhance its frictional characteristics.

Inner tubular member 118 is normally biased to a distalmost longitudinal position relative to outer tubular member 110 as shown in FIG. 2. Coil spring 127, mounted in housing 112, abuts a proximal end of inner tubular member 118 and biases inner tubular member distally. Second implant engaging structure 128 is formed adjacent a distal end of the inner tubular member 118. In the illustrated embodiment, the second implant engaging structure 128 is a hollow polygonal structure having a plurality of flat sides 130 extending from the distal end of inner tubular member 118.

Body portion 104 also includes an inner shaft 132, coaxially mounted at least partially within the inner tubular member 118. Inner shaft 132 is longitudinally rotatable relative to inner tubular member 118 and outer tubular member 110 by wheel 134. As shown, set screw 136 connects wheel 134 to a distal end of inner shaft 132. In a preferred embodiment, the outer periphery of wheel 134 is provided with a friction enhancing surface such as knurling 138.

A second cavity 140 is defined in housing 112 proximal to first cavity 124 and serves to confine wheel 134, and thus inner shaft 132, to limited longitudinal motion relative to outer and inner tubular members 110 and 118, respectively between walls 112c, 112d. Wheels 120 and 134 preferably extend radially beyond at least one outer peripheral surface of house 112 to facilitate actuation by the fingers of a user.

Inner shaft 132 has third implant engaging structure 142 positioned adjacent a distal end (See FIGS. 2 and 6A). In the illustrated embodiment, this structure is threads 144 formed on a distal end of inner shaft 132.

Referring now to FIGS. 2 and 2A, releasable engagement structure 108 of the illustrated embodiment of implant insertion apparatus 100 includes a distal sleeve 146 having an inner surface configured to engage hexagonal projection 148 formed on a proximal end of housing 112.

Proximal sleeve 150 is operatively associated with distal sleeve 146 and includes an internal spring loaded ball system 152 configured to releasable engage an annular channel 154 which extends proximally from hexagonal projection 148. Proximal sleeve 150 is mounted on a distal end of handle portion 102 for relative longitudinal motion between a locked position (FIG. 2) and an unlocked position (FIG. 2A). In the locked position, ball system 152 is forced radially inward into annular channel 154. Spring 156 normally biases proximal sleeve 150 into this locked position. As shown in FIG. 2A, in the unlocked position, proximal sleeve 150 is retracted to release ball system 152 from annular channel 154. This enables the removal of handle portion 102 from the body portion 104 so the handle portion can be attached to and used with other instrumentation necessary for performing the surgical procedure.

Referring to FIGS. 2B and 2C in view of FIG. 1, a versatile feature of the illustrated embodiment is shown. In this preferred embodiment, a distal end portion 158 of outer tubular member 110, which contains first implant engagement structure 114, is interchangeably attached via a friction fit. This allows the user to position another distal end portion 160, such as that shown in FIG. 2C, mounting either a different size (e.g. diameter) implant or configuration of implant engagement structure on the same implant insertion apparatus. Thus, the insertion apparatus can be readily adapted to insert different implants.

Figure 4:
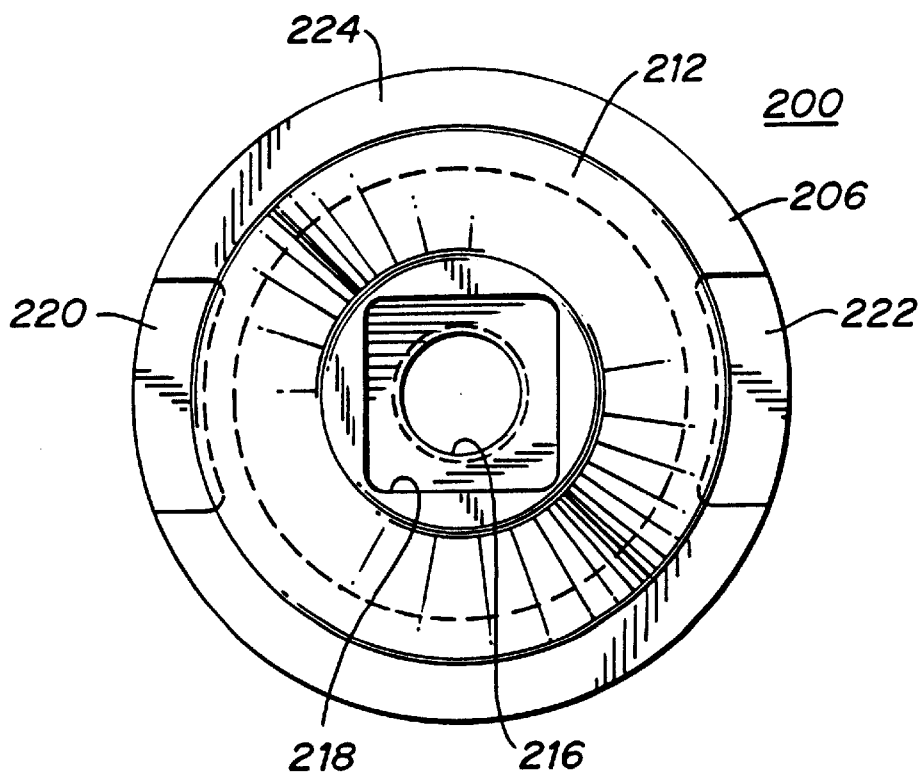
FIG. 4 is an enlarged proximal end view of the implant of FIG. 3 illustrating the structure of the removable end cap.
Figure 5:
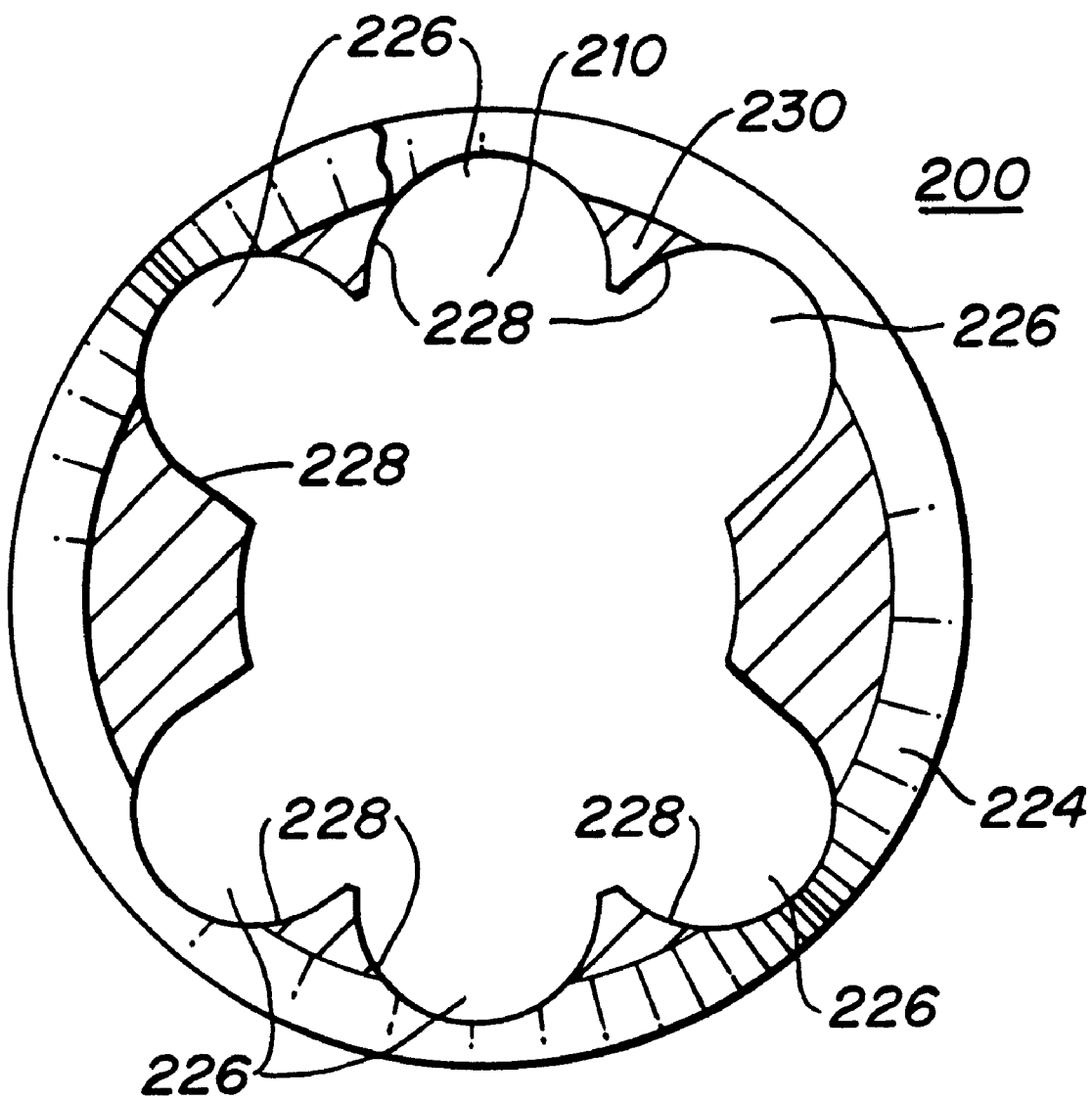
FIG. 5 is an enlarged end view in cross-section of the implant taken along line 5—5 of FIG. 3.
Figure 11:
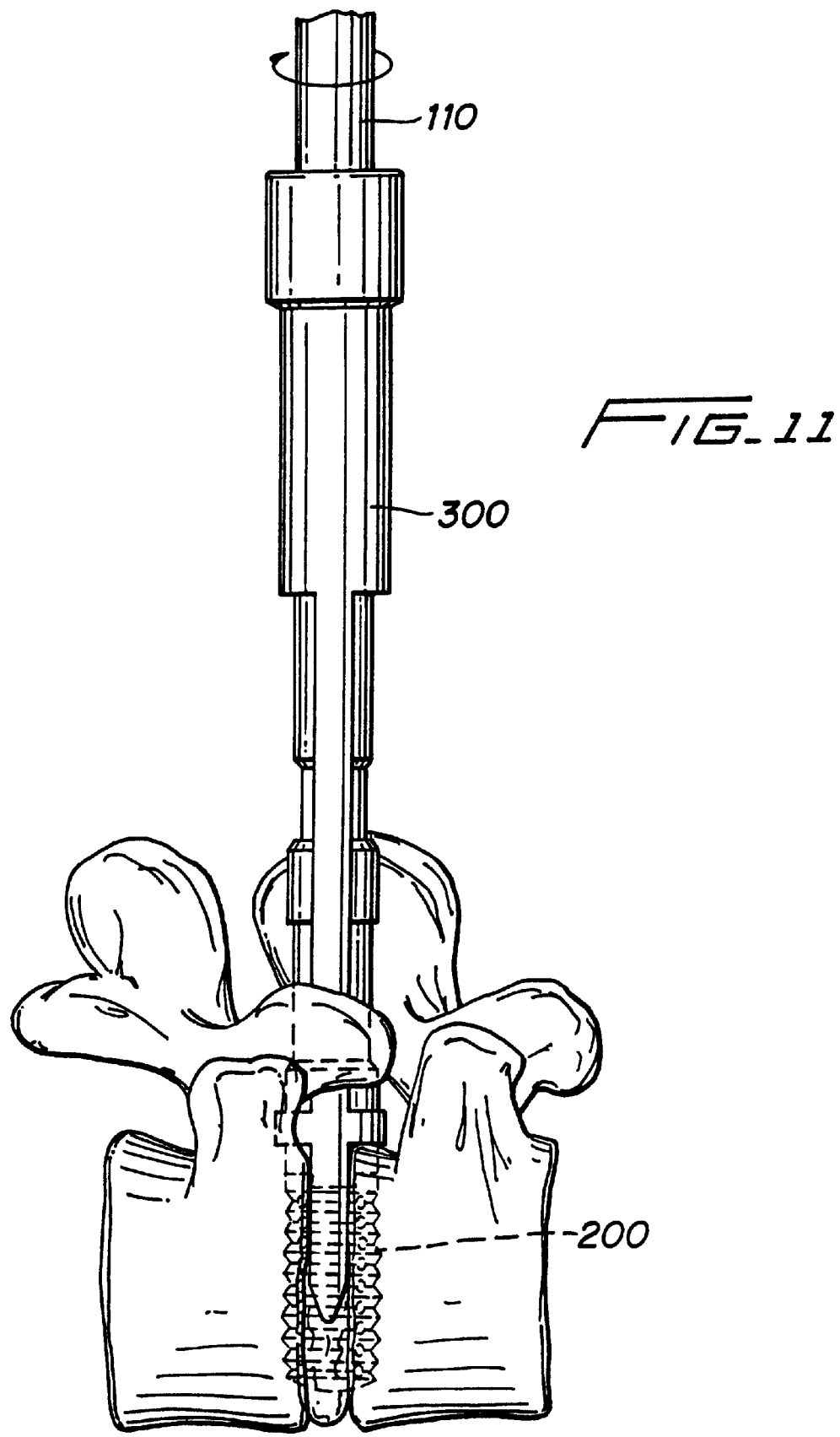
FIG. 11 is a side view illustrating the insertion of the implant of FIG. 7 using the insertion apparatus of FIG. 1.

An implant designed for use in spinal fusion procedures is shown in FIGS. 3–5 and designated generally by the reference number 200. This implant is commonly referred to as a "fusion cage" and, in this embodiment, is specifically configured for a posterior access spinal fusion procedure. Subsequent discussion regarding an exemplary use of the implant insertion tool 100 will be focused on this posterior spinal fusion procedure inserting fusion cage 200. It is contemplated, however, that the disclosed implant insertion tool has broad application in a wide variety of implant insertion procedures beyond either anterior or posterior spinal fusion.

Fusion cage 200 includes a body portion 202 with a closed distal end 204 and a proximal end 206. The distal end 204 is rounded or bull nosed to facilitate insertion of the fusion cage 200 relative to one or more bone structures. The proximal end 206 defines an opening 208 (FIG. 6) which communicates with an internal cavity 210 (FIG. 5) defined by fusion cage 200. In the illustrated embodiment, opening 208 is threaded to receive an end cap 212. This end cap 212 is used to close off the proximal end 206 and to retain bone growth inducing substances, such as bone chips 214 (FIG. 6), packed therein.

Referring to FIG. 4, end cap 212 defines a threaded bore 216 which is configured to receive third implant engaging structure 142 of inner shaft 132 as will be discussed in further detail below. End cap 212 also defines a substantially square depression 218 coaxial with thread bore 216 and configured to receive second implant engaging structure 128 on inner tubular member 118.

The proximal end 206 further defines first and second peripheral indentations 220, 222 which are centered about transverse axis "T". These peripheral indentations 220, 222 are configured to receive first implant engagement structure 114, in this case tabs 116. These indentations may also be used to line up the fusion cage 200 for proper insertion and placement between the adjacent vertebral structure.

A helical thread 224 is formed on the outer peripheral surface of the fusion cage 200. A plurality of apertures 226 are defined by and extend through the fusion cage 200. In the illustrated fusion cage 200, apertures 226 are formed by broaching grooves 228 (FIG. 5) in the internal surface 230 of internal cavity 210. This technique removes material from the valleys between the turns of the thread 224, thus defining apertures 226 to advantageously provide immediate contact between the vertebral body and the bone chips located inside the cage when the cage is positioned in the body.

Referring now to FIGS. 6, 6A and 7, two methods of closing the end cap 212 in the opening 208 of proximal end 206 are illustrated In FIG. 6, bone chips 214 are deposited into internal cavity 210 using forceps. Thereafter, end cap 212 can be manually threaded into opening 208 either by hand or with a socket wrench-type instrument. Alternatively, end cap 212 can be positioned into engagement with second and third implant engaging structure 128, 142 of implant insertion apparatus 100. This is done by positioning the flat sides 130 of second implant engaging structure 128 into square depression 218 of end cap 212. The distal end of inner shaft 132 is then threaded into bore 216 of end cap 212 by rotating wheel 134 (FIG. 1). End cap 212 is then securely engaged by the second and third implant engaging structure 128, 142. The implant insertion apparatus 100 is positioned with the engaged end cap 212 in juxtaposed axial alignment with opening 208 in proximal end 206 of fusion cage 200. Rotation of wheel 120 threads the end cap 212 into the fusion cage 200. As shown, in both methods, packing of the cage occurs outside the body. This facilitates insertion of bone chips since the chips are individually placed with a forceps and lightly tapped, e.g., compacted, inside the cage. This is especially advantageous where access to the cage once implanted is limited and/or with smaller cages such as in cervical applications.

Mounting a packed fusion cage (FIG. 7) onto the insertion apparatus 100 and subsequent insertion into an intervertebral space will now be described with reference to FIGS. 8 through 12. In FIGS. 8A and 8B, the packed fusion cage is positioned in axial alignment with the proximal end of fusion cage 200, aligning tabs 116 with indentations 220, 222; flat sides 130 with square depression 218; and threads 144 with threaded bore 216.

Referring now to FIGS. 9A, 9B, 10A and 10B, fusion cage 200 is moved initially into engagement with inner tubular member 118 such that flat sides 130 are disposed in square depression 218 of end cap 212. Further proximal motion (indicated by the arrows in FIGS. 9A and 9B) of inner shaft 118 relative to inner shaft 132 by either pressing cage 200 against the apparatus or moving wheel 120 proximally brings threads 144 into engagement with threaded bore 216 and tabs 116 of outer tubular member 110 into simultaneous engagement with indentations 220 and 222. (FIG. 10A) Wheel 120 can be slightly rotated to ensure alignment of tabs 116 and indentations 220, 222. Then, wheel 134 is rotated to cause the threaded inner shaft to engage the fusion cage 200 by end cap 212 thus securely mounting the fusion cage 200 on the distal end of the implant insertion apparatus 100 as the cage 200 is pulled proximally via the engagement of the threads.

Thereafter, the implant insertion apparatus 100 is positioned adjacent the implant site (FIG. 11) which typically includes a pretapped bore formed in an intervertebral space between two adjacent vertebra. (Alternately, the fusion cage could be self-tapping.) The implant insertion apparatus 100 may be guided into position using a cannula or C-retractor 300 to facilitate accurate insertion of fusion cage 200. The T-handle 106 is then rotated to rotate outer tubular member 110 to engage threads 224 of the fusion cage 200 (shown in phantom) in the intervertebral space 302.

Figure 12:
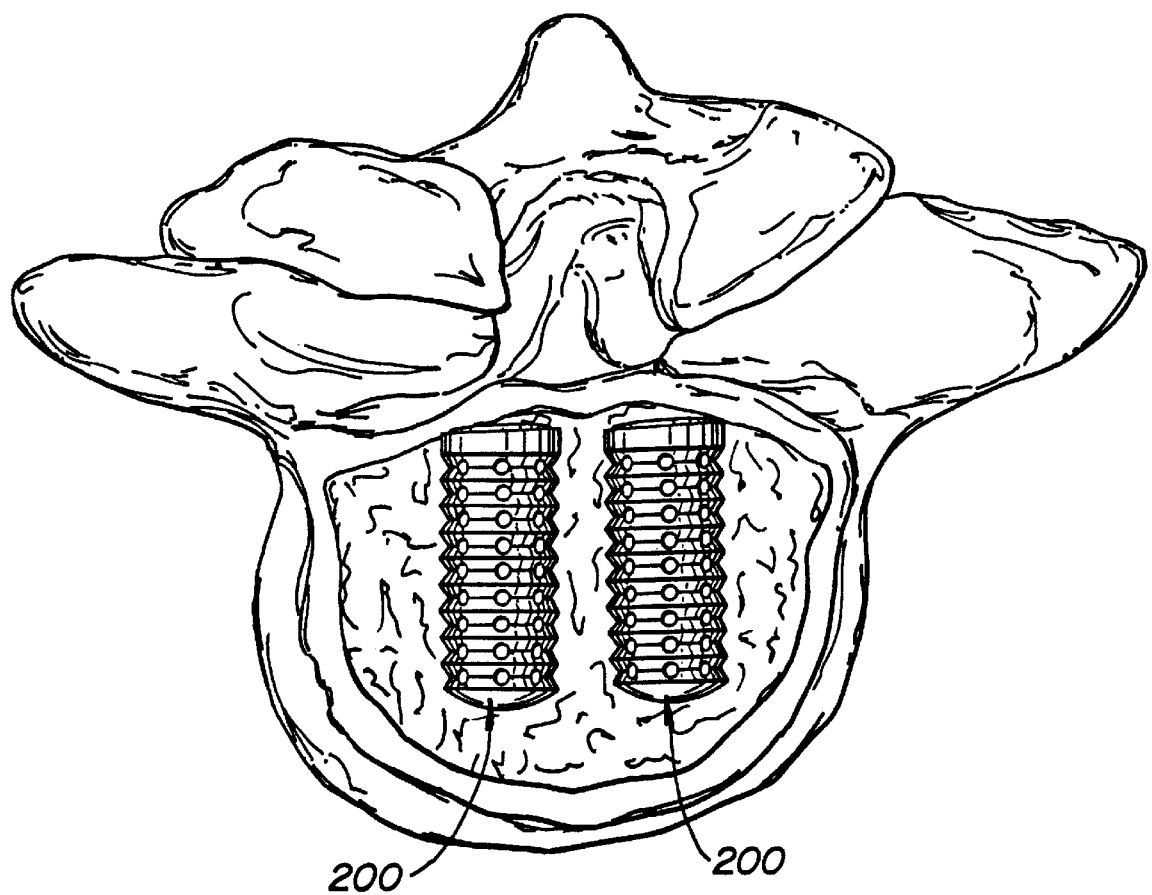
FIG. 12 is an enlarged top view in partial cross-section of a pair of implants in place in the intervertebral space of a lumbar spinal section.

Once the fusion cage 200 is in position, wheel 134 is rotated to disengage treads 144 from threaded bore 216. This releases the implant insertion apparatus 100 from the implanted fusion cage 200. (FIG. 12)

Note that since the fusion cage 200 is grasped and inserted by the apparatus 100 from its open end, once positioned inside the body, the end cap 212 can be removed if the user desires to view or access the bone chips in the internal cavity 210.

The implant insertion apparatus 100 can also be utilized to insert an empty implant such as fusion cage 200 into the intervertebra space and subsequently seal the fusion cage after packing the fusion cage with bone growth inducing substance in vivo. In this procedure, the empty fusion cage is engaged with the first, second and third implant engagement structure 114, 128, 142 and inserted in the same manner outlined above. Once in place in the body, wheel 120 is rotated to remove end cap 212 from body portion 202 and the implant insertion apparatus with attached end cap 212 (FIG. 6A) is removed from the site.

Thereafter, the fusion cage 200 can be packed and the procedure reversed to thread the end cap 212 securely back into place on the body portion 202 using apparatus 100 as described above without affecting the relative position of the body portion 202 at the site. This would avoid the necessity for a separate cap insertion tool since apparatus 100 could serve the dual function of inserting the cage and attaching the end cap.

It will be understood that a wide variety of modifications may be made to the embodiments of the apparatus and methods disclosed herein. For example, the first, second and/or third implant engaging structures can be modified to facilitate engagement with a vast number of implants, both prosthetic and natural. Also, endoscopic, arthroscopic and percutaneous methods of use are easily accommodated. Therefore, the above description should not be construed as limiting, but merely as exemplifications of preferred embodiments. Those skilled in the art will envision other modifications within the scope and spirit of the claims appended hereto.

What is claimed is:

1. A method of inserting an implant comprising the steps of:

providing an apparatus including a handle portion and a body portion attached to the handle portion and defining a longitudinal axis, the body portion including an outer tubular member fixed relative to the handle portion for rotation therewith about the longitudinal axis, the outer tubular member having first implant engaging structure adjacent a distal end, an inner tubular member disposed at least partially within the outer tubular member and mounted for longitudinal motion relative to the outer tubular member and having second implant engaging structure adjacent a distal end and an inner shaft, coaxially mounted at least partially within the inner tubular member for independent rotation relative to the inner and outer tubular members, the inner shaft having third implant engaging structure adjacent a distal end;

providing an implant having a hollow portion with a closed distal end and a removable proximal end cap;

attaching the first, second and third implant engaging structures to the implant; and inserting the implant into a desired surgical location.

2. A method as in claim 1 wherein the implant includes a threaded portion formed on an outer peripheral surface of the hollow closed distal end and the inserting step including rotating the implant into a desired surgical location.

3. A method as in claim 2 wherein the first implant engaging structure includes a pair of tabs positioned on a distal end of the outer tubular member and the attaching step includes engaging the tabs with the hollow closed distal end of the implant.

4. A method as in claim 2 wherein the attaching step includes engaging the second and third implant engaging structure to the proximal end cap of the implant.

5. A method as in claim 1 further comprising the step of loading the implant with bone growth stimulation media.

6. A method as in claim 5 wherein the step of loading the implant is carried out before the implant is inserted.

* * * * *